(12) United States Patent
Gallagher

(10) Patent No.: US 10,401,272 B2
(45) Date of Patent: Sep. 3, 2019

(54) APPARATUS AND METHOD FOR MEASURING FLUID PROPERTIES

(71) Applicant: Hydramotion Limited, Yorkshire (GB)

(72) Inventor: John Gallagher, Yorkshire (GB)

(73) Assignee: Hydramotion Limited, Yorkshire (GB)

( * ) Notice: Subject to any disclaimer, the term of this patent is extended or adjusted under 35 U.S.C. 154(b) by 63 days.

(21) Appl. No.: 15/738,865

(22) PCT Filed: Jun. 30, 2016

(86) PCT No.: PCT/GB2016/051988
§ 371 (c)(1),
(2) Date: Dec. 21, 2017

(87) PCT Pub. No.: WO2017/001861
PCT Pub. Date: Jan. 5, 2017

(65) Prior Publication Data
US 2018/0172573 A1    Jun. 21, 2018

(30) Foreign Application Priority Data
Jun. 30, 2015 (GB) .................................. 1511406.9

(51) Int. Cl.
*G01F 1/84* (2006.01)
*G01N 11/16* (2006.01)
*G01N 11/00* (2006.01)

(52) U.S. Cl.
CPC ........... *G01N 11/167* (2013.01); *G01F 1/849* (2013.01); *G01F 1/8413* (2013.01); *G01N 2011/0073* (2013.01)

(58) Field of Classification Search
CPC ........................................................ G01F 1/84
See application file for complete search history.

(56) References Cited

U.S. PATENT DOCUMENTS

| 4,466,272 A * | 8/1984 | Stansfeld | ............... G01N 9/002 |
| | | | 73/32 A |
| 4,524,610 A * | 6/1985 | Fitzgerald | ............ G01N 11/167 |
| | | | 73/32 A |

(Continued)

FOREIGN PATENT DOCUMENTS

| EP | 0 253 504 A1 | 1/1988 |
| EP | 0 905 488 A2 | 3/1999 |

(Continued)

OTHER PUBLICATIONS

International Search Report and Written Opinion for corresponding Patent Application No. PCT/GB2016/051988 dated Nov. 4, 2016.

*Primary Examiner* — Jewel V Dowtin
(74) *Attorney, Agent, or Firm* — Renner, Otto, Boisselle & Sklar, LLP

(57) ABSTRACT

Apparatus for the measurement of a fluid property is shown generally at (10). The apparatus is typically suitable for the measurement of a property of a fluid (not shown) such as its viscosity, and comprises a tube (12) for the through-flow of fluid to be measured, a torsion bar (14), a magnetic drive coil (16) and a magnetic pick-up coil (18). The tube (12) is mounted within a casing (20), shown in cutaway. An inertial frame (22) is secured to the casing via isolators (not shown). The tube (12) has a web portion (24) supporting inertial masses (26) connected to, and radially spaced from, the tube (12). The tube is connected at each end to pipe fittings (28) via end flanges (30) and seals (32). The single tube (12) has been selectively machined to produce areas (12*a*) of low compliance which effectively form springs. The torsion bar (14) is of relatively low inertia and is fixed at the midpoint of the length of the tube (12). The mass system (24, 26) is of much higher inertia and is fixed to the tube (12) as shown. The tube (12) is then fixed in frame (22) which is of even (Continued)

Figure 1:
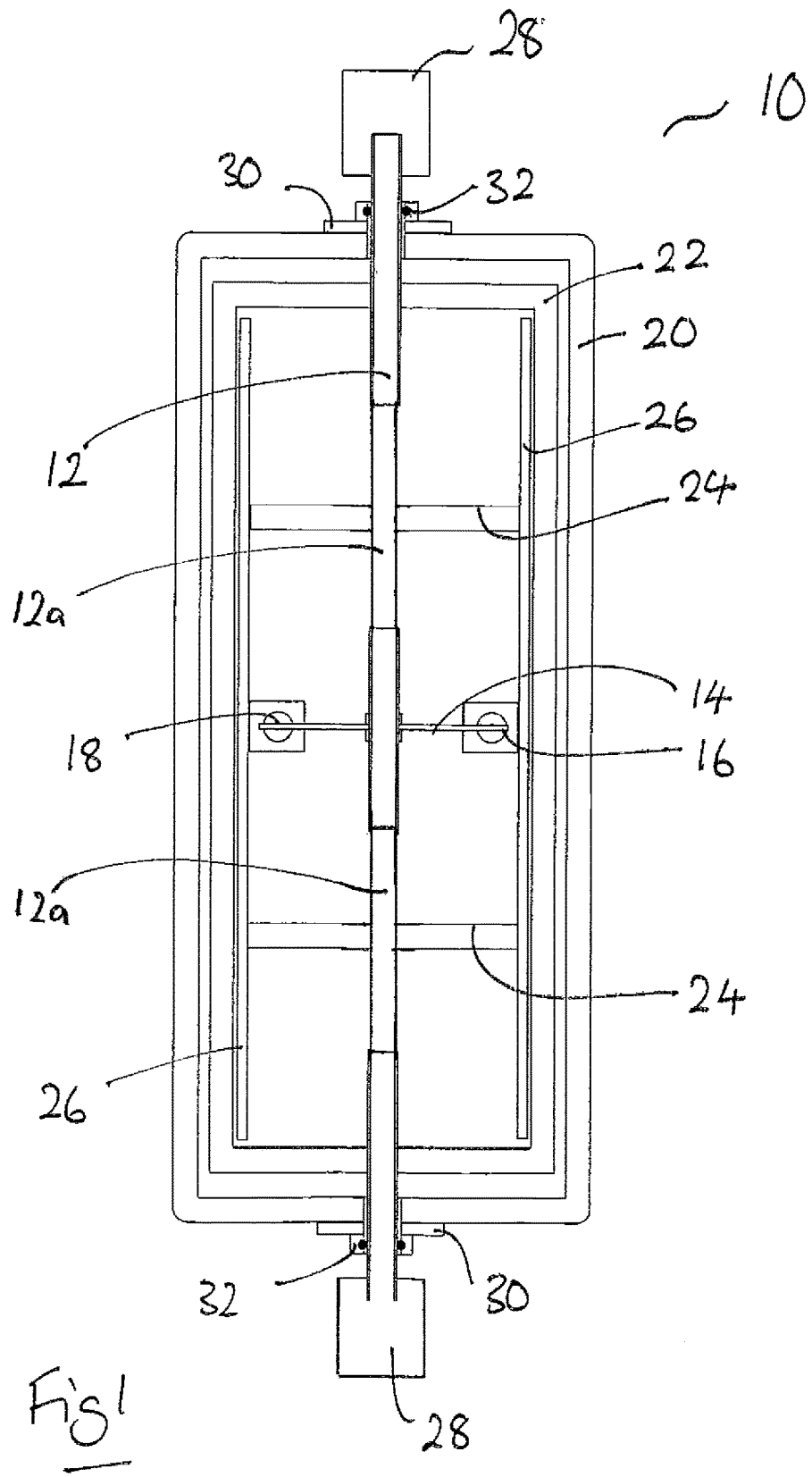

higher inertia, and held in place in casing (20) by means of fixing supports (not shown).

15 Claims, 2 Drawing Sheets

(56) References Cited

U.S. PATENT DOCUMENTS

| | | | |
|---|---|---|---|
| 5,549,009 A * | 8/1996 | Zaschel | G01F 1/8409 |
| | | | 73/861.355 |
| 2001/0039829 A1 | 11/2001 | Wenger et al. | |
| 2003/0097881 A1 | 5/2003 | Schlosser et al. | |
| 2005/0139015 A1 | 6/2005 | Gebhardt et al. | |
| 2005/0268731 A1 | 12/2005 | Hussain et al. | |

FOREIGN PATENT DOCUMENTS

| | | |
|---|---|---|
| JP | H11 23340 A | 1/1999 |
| WO | 2005/010467 A2 | 2/2005 |

* cited by examiner

APPARATUS AND METHOD FOR MEASURING FLUID PROPERTIES

This application is a national phase of International Application No. PCT/GB2016/051988 filed Jun. 30, 2016 and published in the English language, which claims priority to United Kingdom Patent Application No. 1511406.9 filed Jun. 30, 2015, which are hereby incorporated herein by reference.

The present invention relates to apparatus and a method for measuring properties of a fluid, and is concerned particularly with such an apparatus and such a method which use resonance to measure properties of a fluid.

The present invention is defined in the attached independent claims, to which reference should now be made. Further, preferred features may be found in the sub-claims appended thereto.

According to one aspect of the invention, there is provided apparatus for the measurement of fluid properties, the apparatus comprising a resonator system, a driver arranged in use to drive the resonator system into resonant vibration, the resonator system comprising at least a main resonator and an isolating resonator for at least partly isolating the vibration of the main resonator from an exterior, wherein the main resonator and isolating resonator comprise portions of a common hollow tube through which the fluid is arranged to pass in use.

In a preferred arrangement the isolator comprises one or more mass elements connected to, and spaced from, the tube. One or more of the mass elements may be connected to the tube by a connector, which connector may comprise a web. One of more of the mass elements is preferably radially spaced from the tube.

Preferably the isolating resonator is arranged to have substantial resonant frequency separation from the main resonator.

The tube may have one or more reduced stiffness portions. One or more of the reduced stiffness portions of the tube may comprise a portion of tube that has a tube wall of reduced thickness.

The isolating resonator may be formed from the one or more reduced stiffness portions of the tube.

The isolating resonator is preferably formed by one or more portions of the tube that differ from the main resonator in wall thickness of the tube.

Alternatively, or in addition, the isolating resonator may be formed by one or more portions of the tube that differ from the main resonator in length and/or sectional geometry of the tube.

The driver may comprise one or more coils. In a preferred arrangement the driver comprises a driver coil. The apparatus may also comprise a pick up coil. In a preferred arrangement the apparatus comprises a feedback circuit which may include an amplifier.

Preferably the resonant body is arranged in use to vibrate torsionally about an axis generally parallel with and preferably substantially coincident with a longitudinal axis of the tube.

In a preferred arrangement the apparatus comprises a viscosity meter.

According to another aspect of the present invention there is provided a method of measuring a property of a fluid, the method comprising passing the fluid through a hollow tube forming a resonator system arranged in use to be driven to resonant vibration, the resonator system comprising a main resonator and an isolating resonator formed from portions of the hollow tube, and the isolating resonator being arranged in use to at least partly isolate the vibration of the main resonator from an exterior.

Preferably the method comprises vibrating the tube torsionally about an axis substantially coincident with the longitudinal axis of the tube.

The invention may include any combination of the features or limitations referred to herein, except such a combination of features as are mutually exclusive, or mutually inconsistent.

Figure 2:
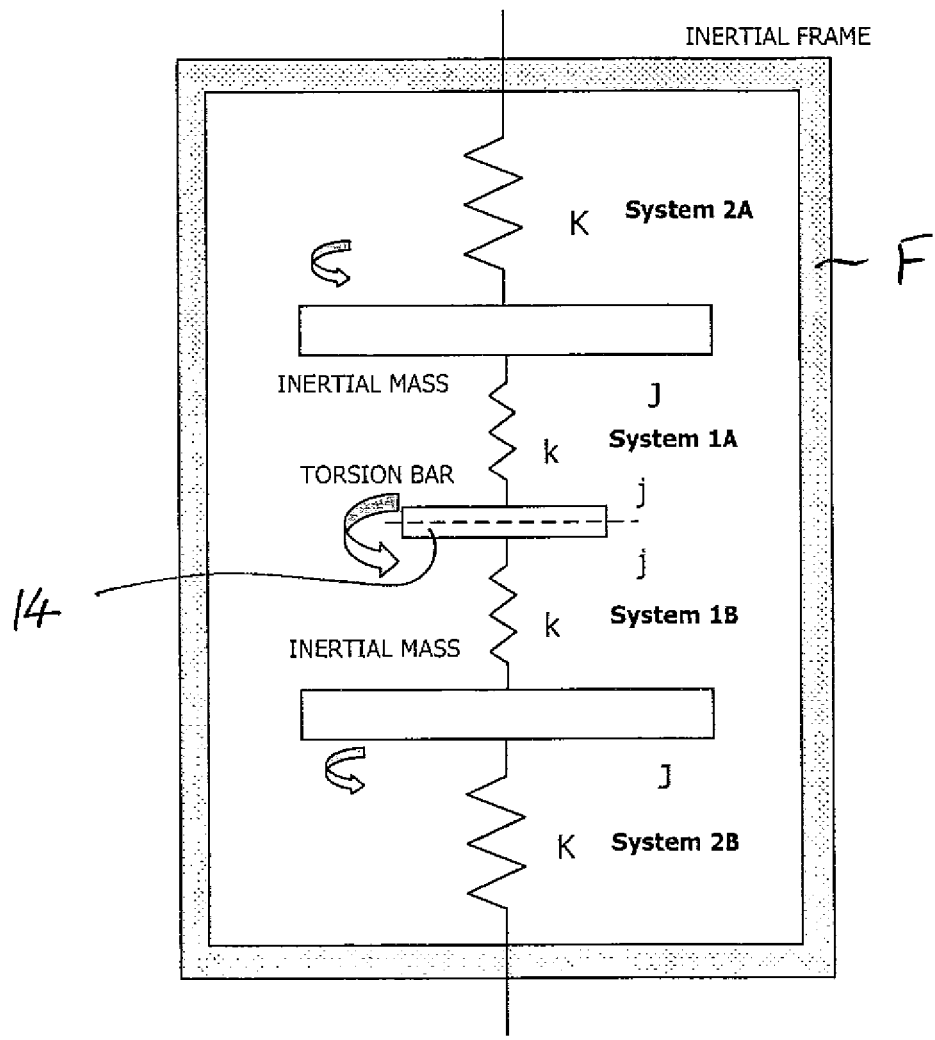

A preferred embodiment of the present invention will now be described, by way of example only, with reference to the accompanying diagrammatic drawings, in which:

FIG. 1 shows in part sectional view a measurement apparatus according to an embodiment of the present invention; and FIG. 2 is a schematic representation of the apparatus of FIG. 1.

Turning to FIG. 1, this shows generally at 10 apparatus for the measurement of a fluid property. The apparatus 10, which is typically suitable for the measurement of viscosity of a fluid (not shown), comprises a tube 12 for the through-flow of fluid to be measured, a torsion bar 14, a magnetic drive coil 16 and a magnetic pick-up coil 18. The tube 12 is mounted within a casing 20, shown in cutaway. An inertial frame 22 is secured to the casing via isolators (not shown).

The tube 12 has a web portion 24 supporting inertial masses 26 connected to, and radially spaced from, the tube 12. The tube is connected at each end to pipe fittings 28 via end flanges 30 and seals 32.

The single tube 12 has been selectively machined to produce areas 12a of low compliance which effectively form springs. The torsion bar 14 is of relatively low inertia and is fixed at the midpoint of the length of the tube 12. The mass system 24, 26 is of much higher inertia and is fixed to the tube 12 as shown. The tube 12 is then fixed in frame 22 which is of even higher inertia, and held in place in casing 20 by means of fixing supports (not shown).

The whole apparatus 10 of FIG. 1 can be analogised to pair of dual spring mass systems mounted back-to back as shown in FIG. 2

Systems 1A and 1B are identical and each consists of a spring k formed by the tube and an inertial mass j formed by half of the torsion bar 14.

Systems 2A and 2B are identical and each consists of a spring K formed by the tube and an inertial mass J comprising the web 24 supporting out-riding masses 26, which are radially disposed to give a high mass moment of inertia. The web is radially stiff but compliant along the axis of the tube to allow for thermal expansion and contraction without creating unwanted stresses on the tube.

The inertial frame F acts a mechanical ground, the intention being that there will be no vibration present to give rise to unwanted damping which will affect the integrity of the measurement and provide an unwanted coupling between external equipment and the resonating structure.

A key advantage of embodiments of the present invention lies in the formation of a vibration isolator, between the main resonator and the inertial frame forming the outer body.

There follows a description of the operation of the apparatus 10.

By means of the electromagnetic coils 16 the torsion bar 14 is driven to induce a torsional twist in the tube 12 which will oscillate at its fundamental resonant frequency or higher modes thereof. The tube 12 is maintained in oscillation using a pickup coil 18 coupled to a positive feedback loop amplifier (not shown). The fundamental frequency of vibration of the tube 12 is defined as:

$$\omega_1 = \sqrt{k/j} = 2\pi f_1$$

A typical value of f1 might be 3000 Hz, for example.

Torsional strain on the resonating tube 12 creates a moment at the point where the tube is connected to the inertial mass J (i.e. the web 24 and the out-riding masses 26). This inertia is substantial and as such will minimise any torsional reaction present at that point, though not completely. The residual vibration can be a source of damping which will influence the quality factor Q of vibration of the system and therefore its effectiveness as a high integrity measuring device will be compromised.

To isolate the residual vibration from any potential damping the inertial mass, J, links with a connecting element, in the form of a second leg 12a of the tube 12 which has a stiffness K. The lower stiffness results from the wall of the tube being machined to have a reduced thickness in the regions 12a. This second system has a resonant frequency given by:

$$\omega_2 = \sqrt{K/J} = 2\pi f_2$$

This is intentionally a much lower frequency than f1 and might typically be 300 Hz for example.

System 2 effectively forms an isolator system of very low transmissibility T given by:

$$T = (f_2/f_1)^2$$

Using the above frequency examples the transmissibility is 0.01 which is sufficient to form an efficient isolator for the main System 1 resonator resulting in a high Q factor with high immunity to process coupling.

Fluid viscosity creates a damping effect on the vibrating tube resulting in a change in mechanical Q-factor. The measurement of mechanical Q-factor and its correlation with damping factor and therefore viscosity is known.

Fluid density alters the resonant frequency of the vibrating tube due to its change in mass—particularly when vibrated in lateral modes. The measurement of mechanical frequency of vibration and its correlation with fluid density is also known.

Phase of vibration of the tube along its longitudinal axis is altered by fluid flow in the tube caused by the Coriolis Effect. The measurement of phase difference along the tube and its correlation with fluid flow rate is known.

By employing a tube structure selectively fashioned into compliant spring zones 12a the resulting resonator provides a highly desirable through-flow device with all the advantage of a clear uninterrupted bore with high operational Q permitting the measurement of multiple fluid properties based on resonant Q, frequency, amplitude or phase.

There are numerous benefits of the apparatus described herein, as compared with prior art apparatus. For example, the apparatus according to an embodiment of the present invention allows continuous in-line measurement of a fluid, whilst providing a clear unobstructed bore. This means that the apparatus is sanitary, non-contaminating, simple to clean and "piggable" (ie free from obstructions thereby allowing a cleaning device or "pig" to pass through unhindered).

High measurement integrity is achieved through effective isolation from external effects using dual spring-mass systems. A high operational Q is realised which allows for measurement stability and high natural rejection of and plant vibration and noise. The torsional mode of vibration is unaffected by entrained air or debris. In addition, the use of flexible webs allows thermal expansion of the flow tube, which is important in some applications.

The unbalanced system described is not affected by temperature variations in resonant structures, is of simple construction, has a lightweight architecture and is scalable from micro-bore to all practical pipe sizes. Furthermore, it is scalable to MEMS and NEMS applications.

Embodiments of the present invention provide a means of creating a resonator system with high isolation from external disturbance by forming a dual resonator arrangement with substantial resonant frequency separation. The resonator system can be used to determine fluid properties of fluid flowing through a tube, including for example viscosity, density and flow rate.

The isolating resonator can conveniently be formed by selective length and/or sectional geometry of the connecting element (K) to the main resonator.

The connecting element can be a tube of selective length, sectional geometry and sectional shape e.g. round, oval, square.

Forming the main resonator and isolating resonator from a single tube presents a smooth, uninterrupted carrier of fluid for the measurement of fluid properties such as rheology, density and flow parameters by existing art.

Selective reduction of wall thickness of a single tube meritoriously favours the performance of the resonator system in isolating the main resonator from external disturbance whilst preserving the benefit of a single smooth bore fluid conduit.

Whilst endeavouring in the foregoing specification to draw attention to those features of the invention believed to be of particular importance, it should be understood that the applicant claims protection in respect of any patentable feature or combination of features referred to herein, and/or shown in the drawings, whether or not particular emphasis has been placed thereon.

For example, several alternatives are possible which do not depart from the scope of the invention, including but not limited to: alternative inertial mass structures, longitudinal vibration modes, lateral vibrational modes and miniaturisation using micro-forming and fabrication techniques.

The invention claimed is:

1. An apparatus for the measurement of fluid properties, the apparatus comprising a resonator system, a driver arranged in use to drive the resonator system into resonant vibration, the resonator system comprising at least a main resonator and an isolating resonator for at least partly isolating the vibration of the main resonator from an exterior, wherein the main resonator and isolating resonator comprise portions of a common hollow tube through which the fluid is arranged to pass in use.

2. The apparatus according to claim 1, wherein the isolator comprises one or more mass elements arranged in use to vibrate with the tube.

3. The apparatus according to claim 1, wherein the one or more mass elements are connected to, and spaced from, the tube.

4. The apparatus according to claim 1, wherein the isolating resonator is arranged to have substantial resonant frequency separation from the main resonator.

5. The apparatus according to claim 1, wherein the isolating resonator is formed from one or more reduced stiffness portions of the tube.

6. The apparatus according to claim 1, wherein the isolating resonator is formed by one or more portions of the tube that differ from the main resonator in wall thickness of the tube.

7. The apparatus according to claim 1, wherein the isolating resonator is formed by one or more portions of the tube that differ from the main resonator in sectional geometry of the tube.

8. The apparatus according to claim 1, wherein the driver comprise one or more coils.

9. The apparatus according to claim 1, wherein the resonators are arranged in use to vibrate torsionally about an axis substantially coincident with a longitudinal axis of the tube.

10. The apparatus according to claim 1, wherein the apparatus comprises a viscosity meter.

11. A method of measuring a property of a fluid, the method comprising passing the fluid through a hollow tube forming a resonator system arranged in use to be driven to resonant vibration, the resonator system comprising a main resonator and an isolating resonator formed from portions of the hollow tube, and the isolating resonator being arranged in use to at least partly isolate the vibration of the main resonator from an exterior.

12. The method according to claim 1, comprising using an isolating resonator having one or more mass elements arranged in use to vibrate with the tube.

13. The method according to claim 11, wherein the method comprises arranging substantial frequency method comprises arranging substantial separation between the isolating resonator and the main resonator.

14. The method according to claim 7, wherein the method comprises vibrating the tube torsionally about an axis substantially coincident with the longitudinal axis of the tube.

15. The method according to claim 11 comprising a method of measuring the viscosity of a fluid.

\* \* \* \* \*